(12) United States Patent
Hou et al.

(10) Patent No.: US 11,933,715 B2
(45) Date of Patent: *Mar. 19, 2024

(54) OZONE DETERIORATION EVALUATION METHOD AND EVALUATION SYSTEM OF VULCANIZED RUBBER MATERIAL

(71) Applicant: THE YOKOHAMA RUBBER CO., LTD., Tokyo (JP)

(72) Inventors: Gang Hou, Hiratsuka (JP); Taro Takahashi, Hiratsuka (JP); Masahiko Miyamoto, Hiratsuka (JP); Naoto Ishii, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 447 days.

This patent is subject to a terminal disclaimer.

(21) Appl. No.: 17/420,295

(22) PCT Filed: Nov. 29, 2019

(86) PCT No.: PCT/JP2019/046745
§ 371 (c)(1),
(2) Date: Jul. 1, 2021

(87) PCT Pub. No.: WO2020/149030
PCT Pub. Date: Jul. 23, 2020

(65) Prior Publication Data
US 2022/0091021 A1 Mar. 24, 2022

(30) Foreign Application Priority Data

Jan. 18, 2019 (JP) .................................. 2019-007342
Jan. 18, 2019 (JP) .................................. 2019-007343

(51) Int. Cl.
*G01N 17/00* (2006.01)
*G01N 33/44* (2006.01)
(Continued)

(52) U.S. Cl.
CPC ......... *G01N 17/002* (2013.01); *G01N 33/445* (2013.01); *G06T 5/73* (2024.01);
(Continued)

(58) Field of Classification Search
CPC ...... G01N 17/002; G01N 33/445; G06T 5/73; G06T 7/0002; G06T 2207/10016; H04N 23/90
See application file for complete search history.

(56) References Cited

U.S. PATENT DOCUMENTS 2,768,068 A * 10/1956 Juve ................... G01N 33/0027
422/403
3,956,234 A * 5/1976 Sagawa ................ C08K 5/3725
524/925
(Continued)

FOREIGN PATENT DOCUMENTS

CN 207163880 U 3/2018
CN 108956436 A 12/2018
(Continued)

OTHER PUBLICATIONS

Jis K 6259-1: 2015, "Determination of Vulcanized Rubber and Thermoplastic Rubber Ozone Resistance", Part 1: Static and dynamic strain testing with partial English translation thereof, First English edition published in Aug. 2016.
(Continued)

*Primary Examiner* — Eric S. McCall
(74) *Attorney, Agent, or Firm* — Carrier, Shende & Associates P.C.; Fulchand P. Shende; Joseph P. Carrier

(57) ABSTRACT

A test sample of a vulcanized rubber material is placed under a preset placement condition in a fixing frame in a test tank having a predetermined ozone concentration, and digital image data is acquired by capturing at a fixed point, over time, with at least one camera device, images of a surface of
(Continued)

the test sample that has been placed in the test tank; and determining a change in a surface state of the test sample between a plurality of points in time by analyzing, with a computation device, the image data that has been acquired. Such evaluation method for evaluating ozone deterioration of a vulcanized rubber material can accurately determine a change over time in ozone deterioration while reducing working man-hours.

7 Claims, 7 Drawing Sheets

(51) Int. Cl.
*G06T 7/00* (2017.01)
*H04N 23/90* (2023.01)

(52) U.S. Cl.
CPC .. *G06T 7/0002* (2013.01); *G06T 2207/10016* (2013.01); *H04N 23/90* (2023.01)

(56) References Cited

U.S. PATENT DOCUMENTS

| | | | | |
|---|---|---|---|---|
| 3,978,021 | A * | 8/1976 | Sagawa | C08K 5/3725 524/925 |
| 4,052,363 | A * | 10/1977 | Kanagawa | C08K 5/16 524/925 |
| 6,131,435 | A | 10/2000 | Mishima et al. | |
| 2018/0354725 | A1 * | 12/2018 | Hou | B65G 43/02 |
| 2020/0189854 | A1 * | 6/2020 | Hou | B65G 43/02 |
| 2022/0091020 | A1 * | 3/2022 | Hou | G01N 17/002 |
| 2022/0091021 | A1 * | 3/2022 | Hou | G01N 17/002 |
| 2023/0365791 | A1 * | 11/2023 | Kondo | C08K 5/14 |
| 2023/0367487 | A1 * | 11/2023 | Kojima | G06F 3/0619 |

FOREIGN PATENT DOCUMENTS

| | | |
|---|---|---|
| JP | H04-109142 A | 4/1992 |
| JP | H09-329595 A | 12/1997 |
| JP | 2003-207419 A | 7/2003 |
| JP | 2014-126370 A | 7/2014 |
| JP | 2015-219049 A | 12/2015 |
| JP | 2017-166942 A | 9/2017 |

OTHER PUBLICATIONS

Ishida et al., "Study on remote moniter of weatherproof examination machinery", Report of Saitama Industrial Technology Center, vol. 5, Jun. 21, 2007, pp. 49-52—cited in the PCT/ISA/210 of PCT/JP2019/046745.

* cited by examiner

US 11,933,715 B2

OZONE DETERIORATION EVALUATION METHOD AND EVALUATION SYSTEM OF VULCANIZED RUBBER MATERIAL

TECHNICAL FIELD

The present invention relates to an evaluation method and an evaluation system for evaluating ozone deterioration of a vulcanized rubber material, and particularly relates to an evaluation method and an evaluation system for evaluating ozone deterioration of a vulcanized rubber material which can accurately determine a change over time in ozone deterioration while reducing working man-hours.

BACKGROUND ART

So-called ozone cracks occur in various vulcanized rubber products such as tires. When ozone cracks become large, the performance and service life of the rubber product are affected. As a method for evaluating the ozone deterioration of vulcanized rubber, a static ozone deterioration test that is specified in JIS K 6259-1: 2015, "Determination of Vulcanized Rubber and Thermoplastic Rubber Ozone Resistance" is widely known. In this test method, a test coordinator checks the deterioration state of a test sample disposed under a predetermined ozone concentration atmosphere at predetermined time intervals. That is, the presence or absence of cracks in the surface of the test sample, the state of the cracks, the size of the cracks, and the like need to be recorded at predetermined time intervals by the test coordinator. In addition, due to a difference in sensory judgment between test coordinators, variations in the evaluation results of ozone resistance occur.

A method for quantitatively evaluating ozone deterioration of vulcanized rubber has been proposed (see, for example, Patent Document 1). In the evaluation method proposed in Patent Document 1, a vulcanized rubber test piece, which has been elongated to a certain degree, is exposed to an ozone atmosphere for a predetermined amount of time, and then the surface state of the test piece is observed with an optical microscope or the like while the test piece is kept in an elongated state. Then, after specifying an image capture region of the surface of the test piece, images of the image capture region are captured by a video camera or the like. Next, the ratio of the area occupied by ozone cracks to the area of the image capture region is calculated by processing the captured images (upper left column to upper right column on page 2 of the specification) . In this method, a quantitative change in the area in which ozone cracks have occurred can be determined. However, it is necessary to observe the surface state of the test piece with a microscope or the like. In addition, when performing observation with a microscope or the like, it also becomes necessary to remove the test piece from a test tank filled with ozone. Therefore, there is room for improvement in the determination of a change over time in ozone deterioration while reducing the number of working man-hours.

CITATION LIST

Patent Literature

Patent Document 1: JP H04-109142 A

SUMMARY OF INVENTION

Technical Problem

An object of the present invention is to provide an evaluation method and an evaluation system for evaluating ozone deterioration of a vulcanized rubber material that can accurately determine a change over time in ozone deterioration while reducing the number of working man-hours.

Solution to Problem

In order to achieve the object described above, a method, for evaluating ozone deterioration of a vulcanized rubber material of the present invention, in which a test sample of a vulcanized rubber material is placed under a preset placement condition in a test tank having a predetermined ozone concentration and a change over time in a surface state of the test sample is determined, includes acquiring image data, which is digital data, by capturing at a fixed point, over time, with at least one camera device, images of a surface of the test sample that has been placed in the test tank; and determining a change in the surface state of the test sample between a plurality of points in time, based on the image data.

A system, for evaluating ozone deterioration of a vulcanized rubber material, in which a test tank is maintained at a predetermined ozone concentration and a fixing frame enables placement of a test sample of a vulcanized rubber material under a preset placement condition in the test tank, includes at least one camera device configured to acquire image data, which is digital data, by capturing at a fixed point, over time, images of a surface of the test sample that has been placed in the test tank; a storage unit into which the image data is input; and a computation device configured to execute a predetermined image data processing program, a degree of change in a surface state of the test sample between a plurality of points in time being calculated by the computation device, based on the image data.

Advantageous Effects of Invention

According to the present invention, with the test sample of the vulcanized rubber material to be evaluated disposed in the test tank having a predetermined ozone concentration, digital image data is acquired by capturing at a fixed point, over time, images of the surface of the test sample by using at least one camera device. Then, the change in the surface state of the test sample between a plurality of points in time is determined on the basis of the acquired image data, so there is no need for the test sample to be removed from and placed into the test tank each time the surface state of the test sample is to be checked. In addition, observation of the surface of the test sample with a microscope or the like is also unnecessary. Furthermore, a change over time in the surface state of the test sample can be determined based on each of the acquired digital image data. Therefore, according to the present invention, it is possible to accurately evaluate a change over time in ozone deterioration while reducing the number of working man-hours.

DESCRIPTION OF EMBODIMENTS

Hereinafter, an evaluation method and an evaluation system for evaluating ozone deterioration of a vulcanized rubber material according to embodiments of the present invention will be described with reference to the drawings.

Figure 1:
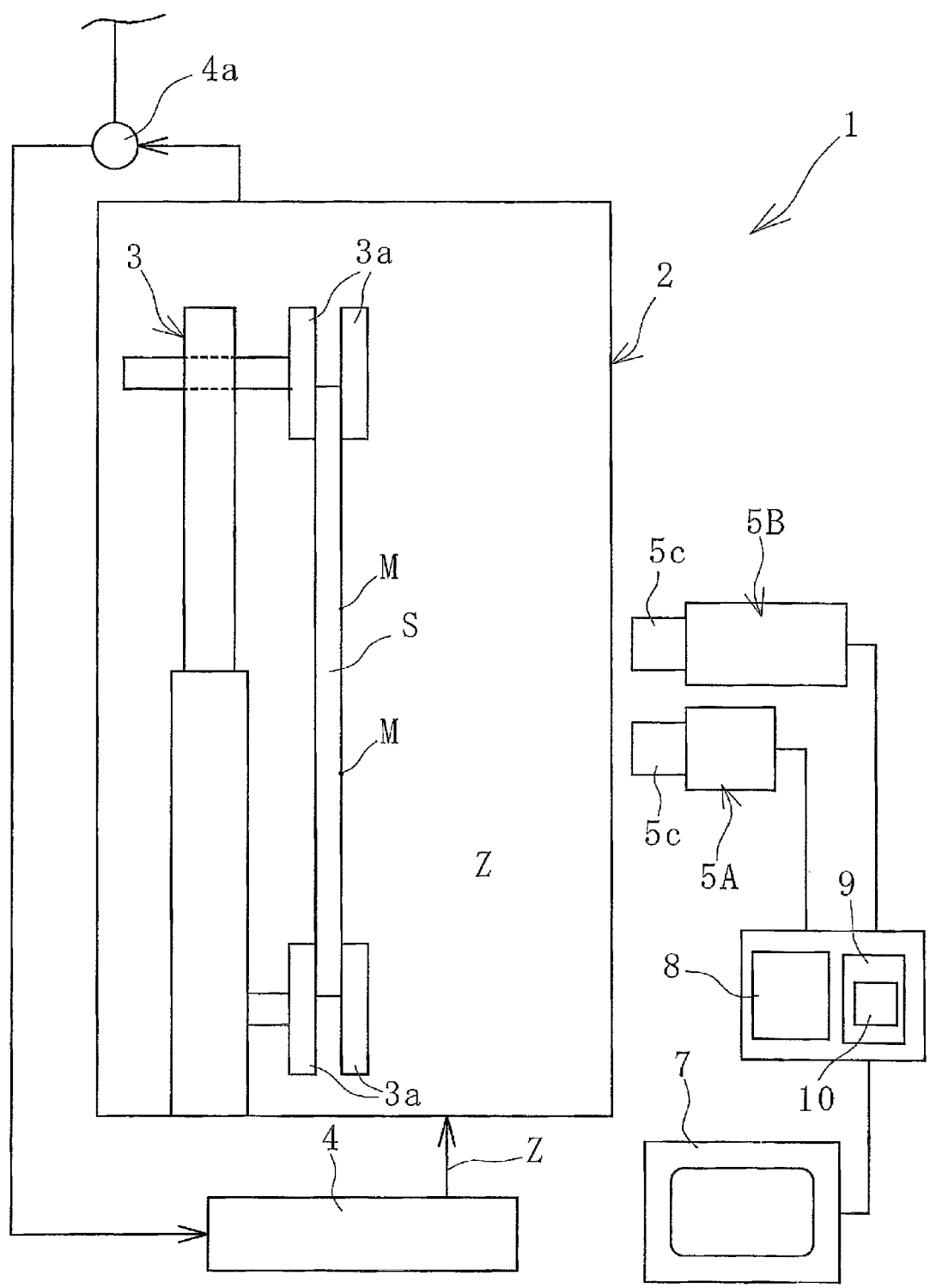
FIG. 1 is an explanatory diagram illustrating an evaluation system of the present invention for evaluating ozone deterioration of a vulcanized rubber material with a test tank viewed from the side.
Figure 2:
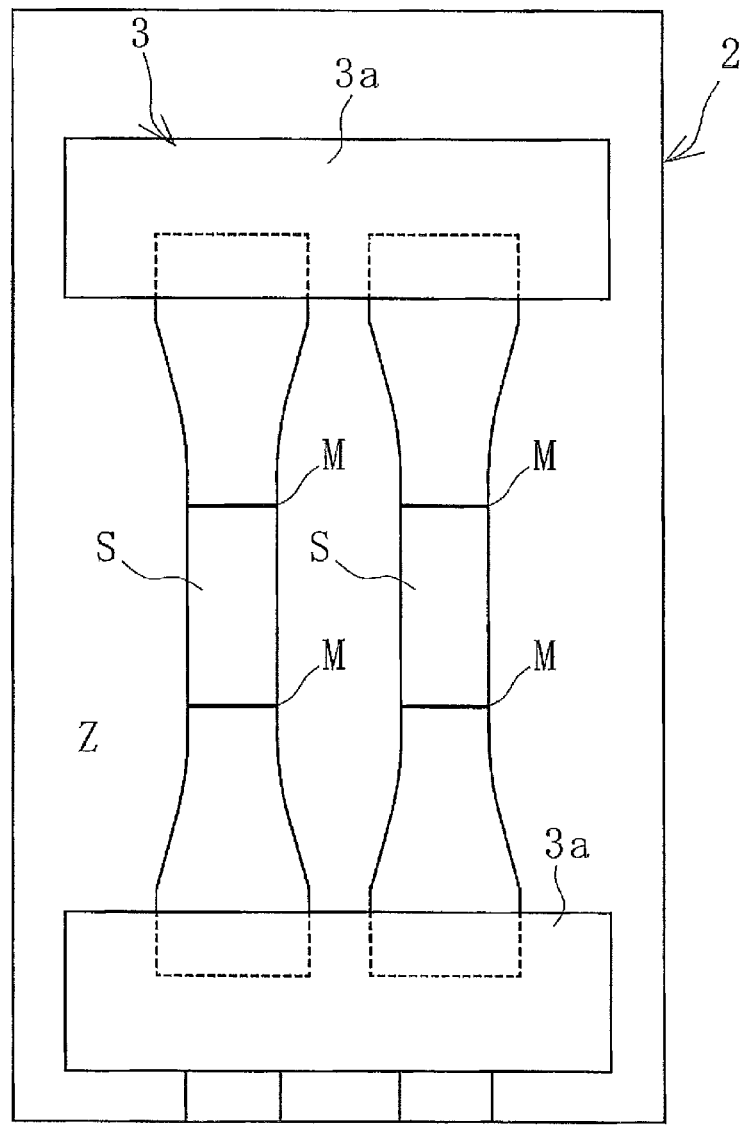
FIG. 2 is an explanatory diagram illustrating a front view of the inside of the test tank in FIG. 1.
Figure 3:
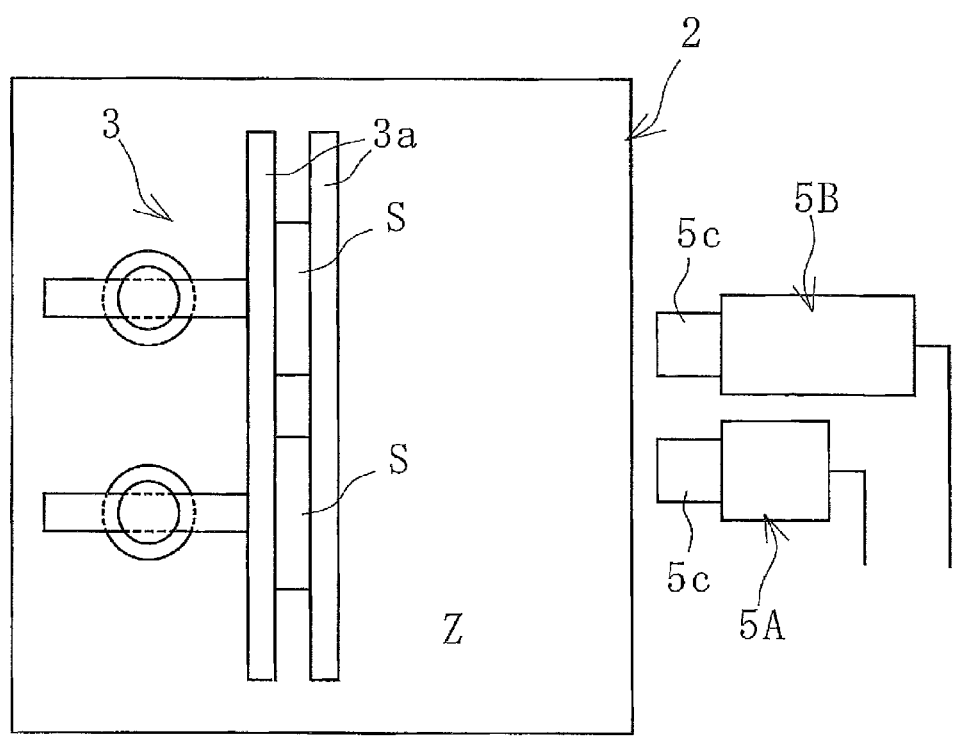
FIG. 3 is an explanatory diagram illustrating a plan view of the inside of the test tank and a camera device illustrated in FIG. 1.

For the evaluation method for evaluating ozone deterioration of a vulcanized rubber material of the present invention, an ozone deterioration evaluation system 1 (hereinafter referred to as evaluation system 1) of the present invention exemplified in FIGS. 1 to 3 is used. The evaluation system 1 includes a test tank 2, a fixing frame 3 to which a test sample S of a vulcanized rubber material to be evaluated is attached, and an ozone injector 4. Furthermore, the system 1 includes at least one camera device 5 (5A, 5B), a storage unit 9 into which digital image data 6x captured by the camera device 5 is input, and a computation device 8 that executes a predetermined image data processing program and the like. A computer including a CPU and a memory may be used as the computation device 8 and the storage unit 9. A monitor 7 is connected to the computer, and the image data 6x (6a, 6b, 6c, . . . ), a calculation result from the computation device 8, and the like are displayed on the monitor 7.

A sample having any of various dumbbell shapes defined in JIS can be used as the test sample S. Alternatively, a cut sample of an actual rubber product, an approximate model of a rubber product, or the like can be used. It is preferable to attach markers M to the surface of the test sample S. As the markers M, for example, markings in a color different from the color of the surrounding surface are used. A tensile strain generated in the test sample S can be easily determined by attaching the markers M at positions separated by a predetermined interval and by checking a separation distance between the markers M. In this embodiment, two test samples S are attached to the fixing frame 3, and the ozone resistances of the two test samples S are measured at the same time; however, there may be one test sample S or a plurality of test samples S. In a case where the ozone resistances of a plurality of test samples S are to be measured at the same time, the test samples S may have the same or different specifications.

The test tank 2 is a container, the inside of which can be sealed, and ozone Z is supplied from the ozone injector 4 such that the ozone concentration in the test tank 2 can be set to a desired concentration. For example, the ozone injector 4 is installed in a circulation path through which the ozone Z is supplied, and the circulation path is provided with an exhaust pipe or the like via an exhaust cleaning filter or a switching valve 4a. Among wall surfaces of the test tank 2, a transparent resin or glass is used for a region facing the camera device 5 (the region required in order for the camera device 5 to capture an image of the surface of the test sample S).

The fixing frame 3 enables placement of the test sample S under a preset placement condition. In this embodiment, both longitudinal end portions of the test sample S are clamped by gripping parts 3a. For example, by attaching and fixing the test sample S to the fixing frame 3, the test sample S is maintained in a state in which a predetermined tensile strain is applied to the test sample S. Alternatively, a predetermined bending strain is applied to the test sample S to maintain the test sample S in a bent state. It is preferable to set the tensile strain applied to the test sample S in accordance with the test method of JIS K 6259-1: 2015. The test sample S may also be placed in a state (form) that corresponds to the state in which a rubber product is actually used.

The camera device 5 acquires the image data 6x by capturing at a fixed point, over time, images of the surface of the test sample S that has been placed in the test tank 2. In this embodiment, two types of a camera device are provided, namely, a still image camera device 5A and a video camera device 5B. The camera devices 5A, 5B may be set to capture images of the same region of the surface of the test sample S. For example, the region between the markers M is set to be the image capture region. One or both of the camera devices 5A, 5B can be a plurality of cameras.

A predetermined image data processing program is installed in the storage unit 9, and a database 10, in which the image data 6x is stored, is stored in the storage unit 9. An example of the image data processing program is a program that identifies and calculates the disposition and area of each degree of shade (color) in the image data 6x. A region in which an ozone crack Cr (hereinafter referred to as crack Cr) occurs and a region in which a crack Cr does not occur on the surface of the test sample S differ in terms of shade (color) in the image data 6x. In general, a region in which a crack Cr occurs is darker than a region in which a crack Cr does not occur. Therefore, by executing this program by using the computation device 8, a region in which a crack Cr occurs and a region in which a crack Cr does not occur are distinguished from each other based on shade (color) in the image data 6x, and the disposition and area thereof are identified and calculated.

In this embodiment, the image data processing program includes a sharpening program for the image data 6x. This sharpening program performs processing such as increasing definition or refinement of the image data 6 and improving contrast so as to make it easy to see the image data 6x that is difficult to see. As a result, it becomes easy to distinguish between a region in which a crack Cr occurs and a region in which a crack Cr does not occur based on shade (color) in the image data 6x, which is advantageous for identifying and calculating the disposition and area of a crack Cr with high accuracy.

Next, an example of a procedure for evaluating ozone deterioration of a test sample S will be described.

As illustrated in FIGS. 1 to 3, test samples S are placed under a preset placement condition inside the test tank 2 having a predetermined ozone concentration. The inside of the test tank 2 is maintained at a predetermined ozone concentration. It is preferable to set the maintained ozone concentration to 500±50 ppb (50±5 pphm), 250±50 ppb (25±5 pphm), 1000±100 ppb (100±10 pphm), and 2000±200 ppb (200±20 pphm) in accordance with the test method of JIS K 6259-1: 2015. It is also possible to set the ozone concentration to one that approximates the conditions in which a rubber product is actually used.

The internal temperature and internal humidity of the test tank 2 are set to appropriate desired ranges. It is preferable that these conditions conform to the test method of JIS K 6259-1: 2015. Therefore, it is preferable that the internal temperature of the test tank 2 be set to 40±2° C. and the relative humidity at the internal temperature be 65% or less;

however, it is also possible to set the internal temperature and the internal humidity to those that approximate the conditions in which a rubber product is actually used.

Then, images of the surface of the test sample S, which has been placed inside the test tank 2, are captured at a fixed point, over time, by at least one camera device 5, and the image data 6x is acquired. The image data 6x can be acquired 2, 4, 8, 24, 48, 72, and 96 hours after the start of testing in conformance with the test method of JIS K 6259-1: 2015; however, the time interval at which the image data 6x is acquired can be arbitrarily set. The still image camera device 5A can be set to acquire the image data 6x at an interval of 10 minutes or at an interval of one hour, for example. The video camera device 5B can be set to acquire the image data 6x successively, for example.

The image data 6x acquired by the camera device 5 (5A, 5B) is successively input to the storage unit 9 and stored therein. The image data 6x that has been input to the computation device 8 is displayed on the monitor 7.

Figure 4:
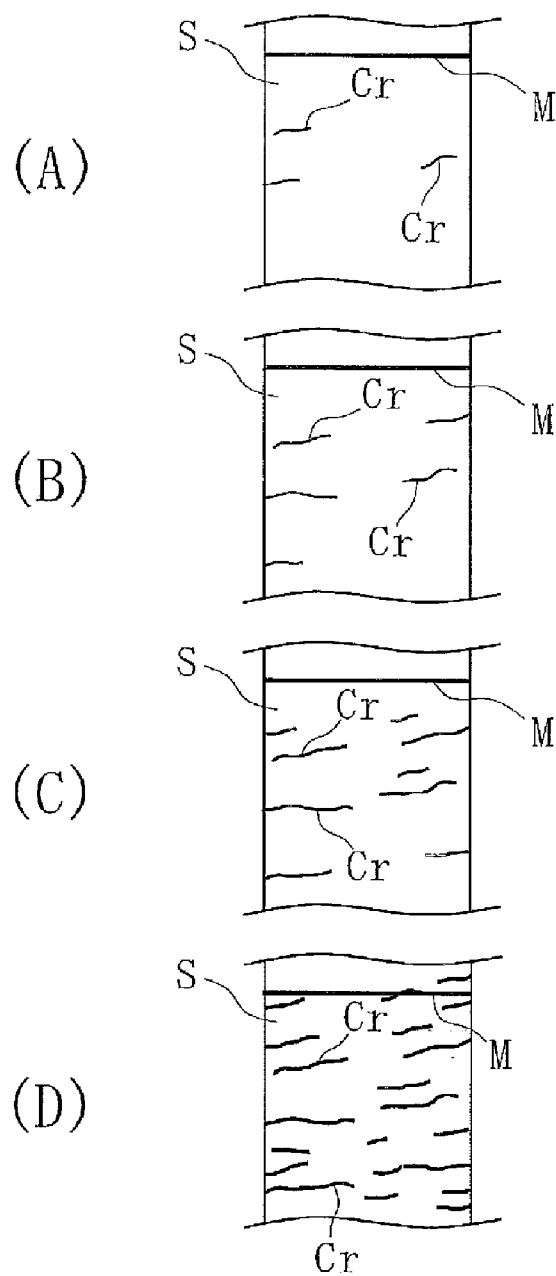
FIG. 4 is an explanatory diagram illustrating a front view of a change over time in a surface of a test sample.

As a result of keeping the test sample S under a predetermined ozone concentration, the chemical bonds between the rubber molecules of the test sample S are broken. Consequently, as illustrated in FIG. 4, the surface state changes because cracks Cr occur on the surface of the test sample S. FIG. 4 illustrates image data 6a, 6b, 6c, and 6d acquired in the chronological order of (A), (B), (C), and (D), respectively.

Thus, based on the acquired image data 6x, the change in the surface state of the test sample S between the plurality of points in time is determined. For example, as the change in the surface state of the test sample S, at least one of the determination items among the total number of cracks Cr that have occurred per unit area, the total area of cracks Cr that have occurred per unit area, the maximum length of cracks Cr that have occurred, the average length of cracks Cr that have occurred, the minimum length of cracks Cr that have occurred, and the length (or area) of a specific one or two cracks Cr is calculated by the computation device 8 on the basis of the image data 6x.

Figure 5:
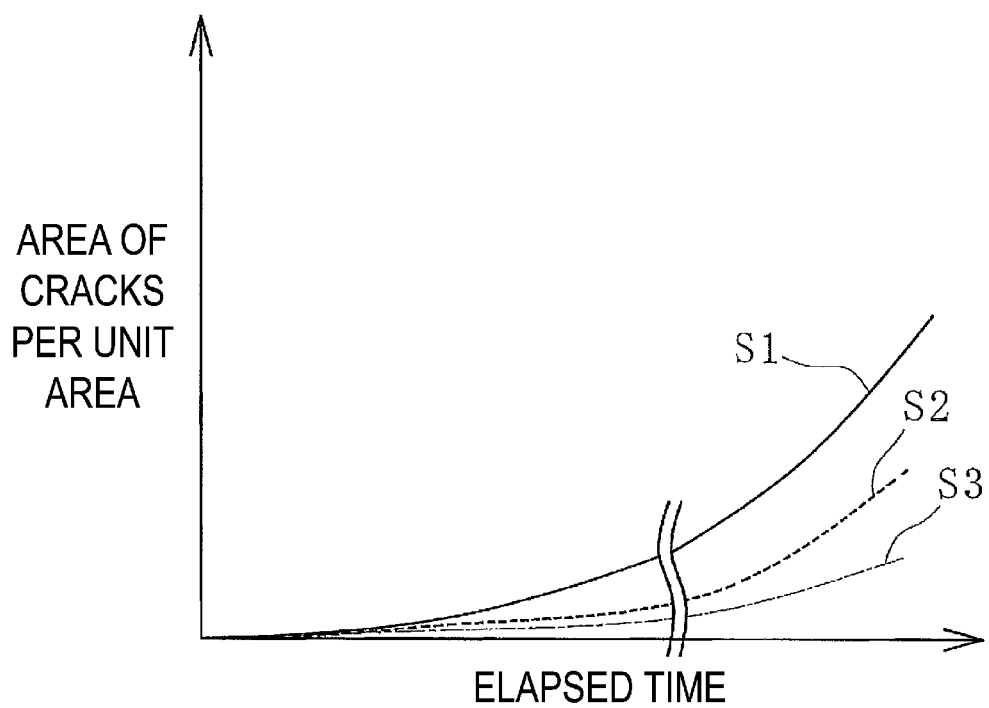
FIG. 5 is a graph illustrating a change over time in the area of cracks that have occurred.

FIG. 5 illustrates the change over time in the total area of the cracks Cr that have occurred per unit area of the test samples S (S1, S2, S3) having different rubber specifications. In this way, it is possible to acquire a computation result by the computation device 8 for a desired determination item.

As described above, the image data 6x is acquired by capturing at a fixed point, over time, images of the surface of the test sample S while the test sample S remains placed inside the test tank 2 having a predetermined ozone concentration. Then, since the change in the surface state of the test sample S between a plurality of points in time is determined on the basis of the acquired image data 6x, it is not necessary to remove the test sample S from and place the test sample S into the test tank 2 each time the surface state of the test sample S is to be checked. Observation of the surface of the test sample S with a microscope or the like is not required.

Since the image data 6x is digital data that is easy to analyze, a change over time in the surface state of the test sample S can be determined by analyzing the image data 6x acquired at different points in time. Therefore, according to the present invention, it is possible to accurately determine a change over time in the ozone deterioration of the vulcanized rubber material forming the test sample S while reducing the number of working man-hours.

Figure 6:
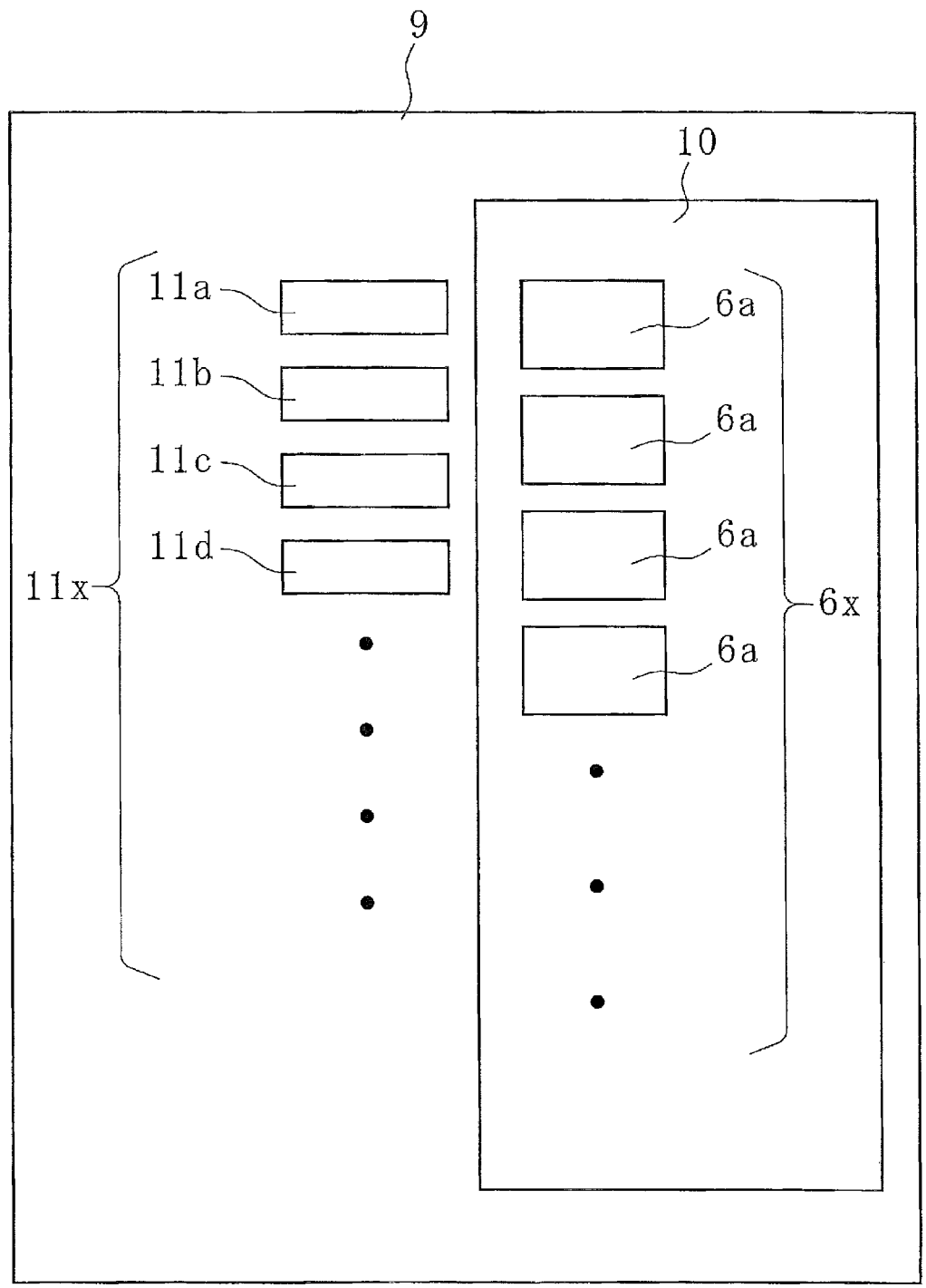
FIG. 6 is an explanatory diagram schematically illustrating data stored in a storage unit.

As illustrated in FIG. 6, each of the image data 6x is stored in the database 10 of the storage unit 9. The storage unit 9 stores indication data 11x (11a, 11b, 11c, ...) indicating the degree of progression of ozone deterioration. Then, it is possible to automatically determine the degree of progression of ozone deterioration with respect to the surface state of the test sample S in each of the image data 6x on the basis of the indication data 11x by comparing each of the image data 6x and the indication data 11x by using the computation device 8.

As the indication data 11x, for example, the indicator described in the method for evaluating cracks in an annex (standard) of JIS K 6259-1: 2015 is used. In other words, image data corresponding to the 15 classifications of A-1 to A-5, B-1 to B-5, and C-1 to C-5 described in this application is stored as the indication data 11x in the storage unit 9. The computation device 8 selects the indication data 11x having the highest degree of matching with each of the image data 6x. Accordingly, the surface state of the test sample S in the image data 6x is determined to be the degree of progression of ozone deterioration indicated by the indication data 11x selected to have the highest similarity between images.

When two types of a camera device, namely, the video camera device 5A and the still image camera device 5B, are used as the camera device 5, it becomes easier to determine the state and degree of change in ozone deterioration in more detail. Similarly, in order to determine the state and degree of change in ozone deterioration in more detail, the degree of change in the surface state of the test sample S between a plurality of points in time is preferably determined using processed data obtained by performing sharpening processing on each of the image data 6x.

Figure 7:
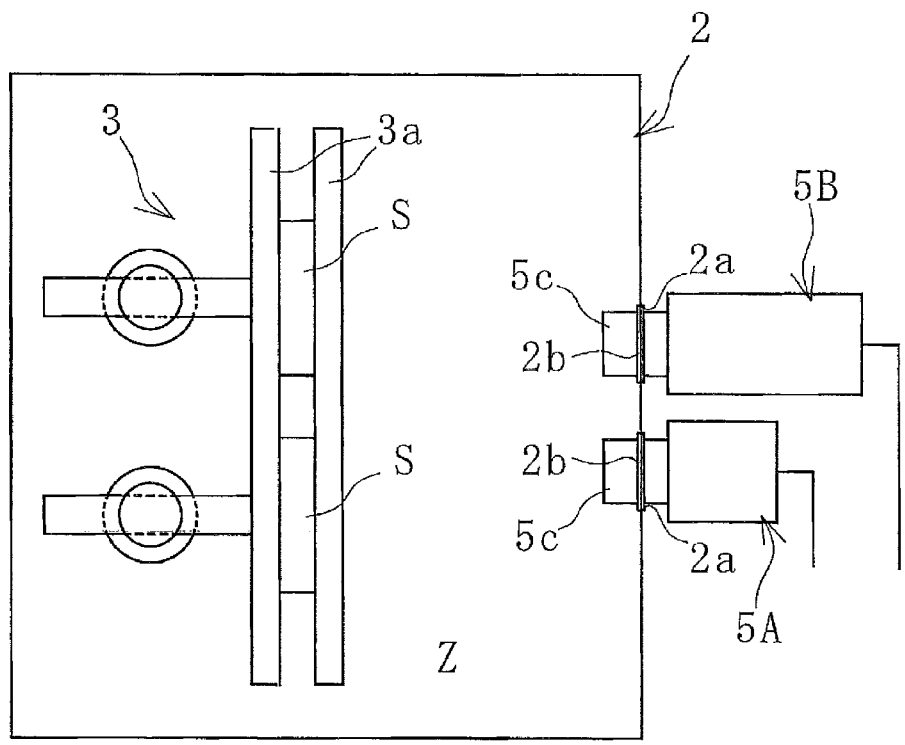
FIG. 7 is an explanatory diagram illustrating a plan view of a modified example of the test tank illustrated in FIG. 3.

In a case where a wall surface of the test tank 2 is interposed between the camera device 5 and the test sample S, noise may be included in the image data 6x due to reflection of light from the wall surface and the like. Thus, as illustrated in FIG. 7, a through hole 2a can be formed in the test tank 2, and an image capturing lens portion 5c of at least one camera device 5 can be inserted into the through hole 2a from the outside to the inside of the test tank 2. A gap between an outer peripheral surface of the image capturing lens portion 5c and the through hole 2a is sealed with a sealing material 2b.

In this embodiment, the body of the camera device 5 is not disposed inside the test tank 2. This is advantageous in that sharper image data 6x is acquired while preventing ingress of the ozone Z into the body of the camera device 5. In the case of the test tank 2 illustrated in FIG. 7, a non-transparent material can be used for all the wall surfaces of the test tank 2.

The image data 6x can be successively input and stored in the storage unit 9 installed in a management office or the like away from the test tank 2 and the camera device 5, via the Internet or the like. As a result, a change over time in the ozone deterioration of the surface of the test sample S (vulcanized rubber material) can be determined in the management office or the like.

REFERENCE SIGNS LIST

1 Evaluation system
2 Test tank
2a Through hole
2b Sealing material
3 Fixing frame
3a Gripping part
4 Ozone injector
4a Switching valve
5 Camera device 5A Still image camera device
5B Video camera device
5c Image capturing lens portion
6x Image data
7 Monitor
8 Computation device
9 Storage unit
10 Database
11x Indication data
S Test sample
M Marker
Cr Crack
Z Ozone

The invention claimed is:

1. A method, for evaluating ozone deterioration of a vulcanized rubber material, in which a test sample of a vulcanized rubber material is placed under a preset placement condition in a test tank having a predetermined ozone concentration and a change over time in a surface state of the test sample is determined, the method comprising:
   acquiring image data, which is digital data, by capturing at a fixed point, over time, with at least one camera device, images of a surface of the test sample that has been placed in the test tank; and
   determining a change in the surface state of the test sample between a plurality of points in time, based on the image data, to evaluate a change in ozone deterioration of the test sample.

2. The method for evaluating ozone deterioration of a vulcanized rubber material according to claim 1, wherein the at least one camera device comprises a video camera device and a still image camera device.

3. The method for evaluating ozone deterioration of a vulcanized rubber material according to claim 1, wherein the change in the surface state of the test sample between the plurality of points in time is determined using processed data obtained by performing sharpening processing on each of the image data.

4. The method for evaluating ozone deterioration of a vulcanized rubber material according to claim 1, further comprising:
   storing each of the image data in a database of a storage unit; and
   automatically determining, by comparing indication data indicating a degree of progression of ozone deterioration stored in the storage unit and each of the image data by using a computation device, the degree of progression of ozone deterioration with respect to the surface state of the test sample in each of the image data, based on the indication data.

5. The method for evaluating ozone deterioration of a vulcanized rubber material according to claim 1, wherein, as the change in the surface state of the test sample, at least one determination item among a total number of ozone cracks that have occurred per unit area, a total area of ozone cracks that have occurred per unit area, a maximum length of ozone cracks that have occurred, an average length of ozone cracks that have occurred, a minimum length of ozone cracks that have occurred, and a length or area of a specific ozone crack that has occurred is determined.

6. The method for evaluating ozone deterioration of a vulcanized rubber material according to claim 1, wherein a through hole is formed in the test tank, and an image capturing lens portion of at least one of the camera devices is inserted into the through hole from outside to inside the test tank, a gap between an outer circumferential surface of the image capturing lens portion and the through hole is sealed, and the image data is acquired.

7. A system, for evaluating ozone deterioration of a vulcanized rubber material, in which a test tank is maintained at a predetermined ozone concentration and a fixing frame enables placement of a test sample of a vulcanized rubber material under a preset placement condition in the test tank, the system comprising:
   at least one camera device configured to acquire image data, which is digital data, by capturing at a fixed point, over time, images of a surface of the test sample that has been placed in the test tank;
   a storage unit into which the image data is input; and
   a computation device configured to execute a predetermined image data processing program,
   a degree of change in a surface state of the test sample between a plurality of points in time being calculated by the computation device, based on the image data to evaluate a change in ozone deterioration of the test sample.

* * * * *